US008471866B2

(12) United States Patent
Friedman et al.

(10) Patent No.: US 8,471,866 B2
(45) Date of Patent: Jun. 25, 2013

(54) USER INTERFACE AND METHOD FOR IDENTIFYING RELATED INFORMATION DISPLAYED IN AN ULTRASOUND SYSTEM

(75) Inventors: Zvi Friedman, Kiryat Bialik (IL); Sergei Goldenberg, Kiryat-Ata (IL); Peter Lysyansky, Harofe (IL)

(73) Assignee: General Electric Company, Schenectady, NY (US)

( * ) Notice: Subject to any disclaimer, the term of this patent is extended or adjusted under 35 U.S.C. 154(b) by 1563 days.

(21) Appl. No.: 11/429,546

(22) Filed: May 5, 2006

(65) Prior Publication Data

US 2007/0258632 A1 Nov. 8, 2007

(51) Int. Cl.
*G09G 5/00* (2006.01)

(52) U.S. Cl.
USPC ........... 345/619; 345/632; 345/629; 382/164; 382/132

(58) Field of Classification Search
USPC ............................ 345/629, 632; 382/132, 164
See application file for complete search history.

(56) References Cited

U.S. PATENT DOCUMENTS

| | | | | |
|---|---|---|---|---|
| 5,891,045 A | * | 4/1999 | Albrecht et al. | 600/509 |
| 6,053,869 A | | 4/2000 | Kawagishi | |
| 6,674,879 B1 | | 1/2004 | Weisman et al. | |
| 6,694,178 B1 | * | 2/2004 | Soula et al. | 600/523 |
| 7,155,043 B2 | * | 12/2006 | Daw | 382/128 |
| 2002/0068962 A1 | * | 6/2002 | Ferek-Petric | 607/60 |
| 2003/0171668 A1 | | 9/2003 | Tsujino et al. | |
| 2003/0176802 A1 | * | 9/2003 | Galen et al. | 600/523 |
| 2004/0015079 A1 | | 1/2004 | Berger et al. | |
| 2004/0120580 A1 | * | 6/2004 | Sabol et al. | 382/224 |
| 2005/0113680 A1 | * | 5/2005 | Ikeda et al. | 600/425 |
| 2005/0114175 A1 | | 5/2005 | O'Dea et al. | |
| 2006/0023924 A1 | | 2/2006 | Asbeck et al. | |
| 2006/0056691 A1 | * | 3/2006 | Vaz et al. | 382/173 |
| 2006/0235294 A1 | * | 10/2006 | Florin et al. | 600/425 |
| 2006/0241412 A1 | * | 10/2006 | Rinck et al. | 600/431 |
| 2006/0258947 A1 | * | 11/2006 | Olson | 600/523 |
| 2007/0016016 A1 | * | 1/2007 | Haras et al. | 600/431 |
| 2008/0051659 A1 | | 2/2008 | Waki et al. | |

FOREIGN PATENT DOCUMENTS

| | | |
|---|---|---|
| JP | 2006026079 | 2/2006 |
| WO | WO 99/49775 | 10/1999 |
| WO | WO 03/079038 A2 | 9/2003 |
| WO | WO 2004/070350 A2 | 8/2004 |

OTHER PUBLICATIONS http://en.wikipedia.org/wiki/Ct_scan.*

* cited by examiner

*Primary Examiner* — Michelle L Sams
(74) *Attorney, Agent, or Firm* — The Small Patent Law Group; Dean D. Small

(57) ABSTRACT

A user interface and method for identifying related information displayed in an ultrasound system are provided. A medical image display of the ultrasound system includes a first region configured to display a medical image having color coded portions and a second region configured to display non-image data related to the medical image displayed in the first region. The non-image data is color coded to associate the non-image data with the color coded portions of the medical image.

22 Claims, 5 Drawing Sheets

USER INTERFACE AND METHOD FOR IDENTIFYING RELATED INFORMATION DISPLAYED IN AN ULTRASOUND SYSTEM

BACKGROUND OF THE INVENTION

Embodiments of the present invention relate generally to medical imaging systems, and more particularly, to medical imaging systems displaying information in different portions of a divided display screen.

Ultrasound systems are used in a variety of applications and by individuals with varied levels of skill. In many examinations, operators of the ultrasound system provide inputs used by the system to process the information for later analysis. Once processed, the information may be displayed in different formats. For example, the processed information may be displayed in different graphs or charts and/or as static or moving images. Further, the information may be displayed on different screens or on the same screen. Additionally, the information may be combined, for example, multiple traces on a single graph and/or one type of information overlaid on another type of information or image. Thus, multiple pieces of information may be provided on a screen or within a portion of the screen.

The amount of information that may be displayed can be large. Further, the presentation of the information on the screen, for example, the orientation and configuration of the information may make it difficult to distinguish between closely presented information, such as two traces displayed in close proximity on a graph. Additionally, it is often difficult to associate or correlate information displayed on different portions of a screen.

Thus, it may be difficult for a user to review and analyze the information displayed in different portions of a screen. These difficulties add time to the review and analysis process, and accordingly cost to the overall evaluation process. Further, a user may incorrectly view or associate information, which can lead to improper analysis and diagnosis, resulting in improper treatment for a patient.

BRIEF DESCRIPTION OF THE INVENTION

In accordance with an embodiment of the present invention, a medical image display is provided that includes a first region configured to display a medical image having color coded portions and a second region configured to display non-image data related to the medical image displayed in the first region. The non-image data is color coded to associate the non-image data with the color coded portions of the medical image.

In accordance with another embodiment of the present invention, a medical image display is provided that includes data corresponding to a displayed image and displayed in combination with the displayed image, and visual indications associating data in a first region with data in a second region. The visual indications are color coded based on a segmental spatial view of the displayed image.

In accordance with yet another embodiment of the present invention, a method to associate medical information displayed in different regions of a display of a medical imaging system is provided. The method includes color coding data in different regions of the display, associating data in the different regions based on the color coding and displaying at least one visual indication corresponding to the color coded data in the different regions.

DETAILED DESCRIPTION OF THE INVENTION

Exemplary embodiments of ultrasound systems and methods for identifying related information are described in detail below. In particular, a detailed description of an exemplary ultrasound system will first be provided followed by a detailed description of various embodiments of methods and systems for associating and correlating information displayed in different portions of a screen. A technical effect of the various embodiments of the systems and methods described herein include at least one of facilitating the identification and association of different corresponding information displayed on different portions of a display.

It should be noted that although the various embodiments may be described in connection with an ultrasound system, the methods and systems described herein are not limited to ultrasound imaging. In particular, the various embodiments may be implemented in connection with different types of medical imaging, including, for example, magnetic resonance imaging (MRI) and computed-tomography (CT) imaging. Further, the various embodiments may be implemented in other non-medical imaging systems, for example, non-destructive testing systems.

Figure 1:
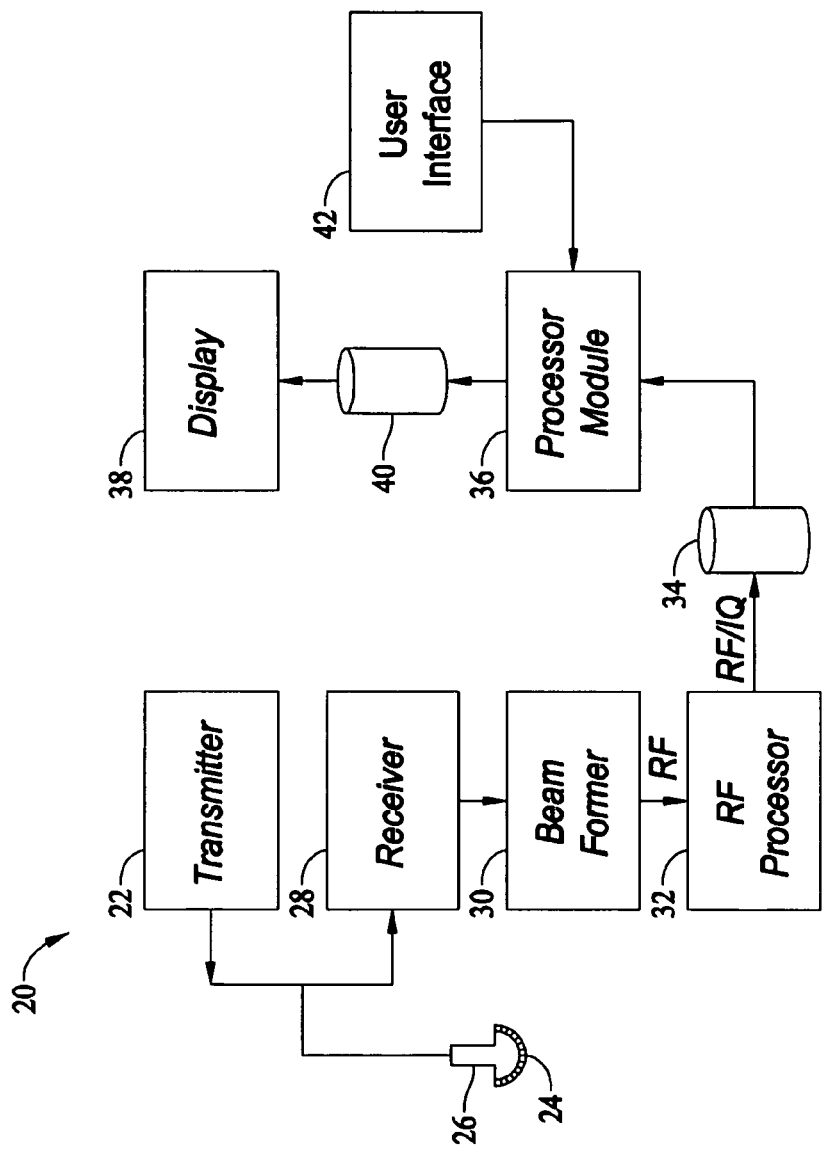
FIG. 1 is a block diagram of a diagnostic ultrasound system formed in accordance with an embodiment of the present invention.

FIG. 1 illustrates a block diagram of an ultrasound system 20, and more particularly, a diagnostic ultrasound system 20 formed in accordance with an embodiment of the present invention. The ultrasound system 20 includes a transmitter 22 that drives an array of elements 24 (e.g., piezoelectric crystals) within a transducer 26 to emit pulsed ultrasonic signals into a body or volume. A variety of geometries may be used and the transducer 26 may be provided as part of, for example, different types of ultrasound probes. The ultrasonic signals are back-scattered from structures in the body, for example, blood cells or muscular tissue, to produce echoes that return to the elements 24. The echoes are received by a receiver 28. The received echoes are provided to a beamformer 30 that performs beamforming and outputs an RF signal. The RF signal is then provided to an RF processor 32 that processes the RF signal. Alternatively, the RF processor 32 may include a complex demodulator (not shown) that demodulates the RF signal to form IQ data pairs representative of the echo signals. The RF or IQ signal data may then be provided directly to a memory 34 for storage (e.g., temporary storage).

The ultrasound system 20 also includes a processor module 36 to process the acquired ultrasound information (e.g., RF signal data or IQ data pairs) and prepare frames of ultrasound information for display on a display 38. The processor module 36 is adapted to perform one or more processing operations according to a plurality of selectable ultrasound modalities on the acquired ultrasound information. Acquired ultrasound information may be processed in real-time during a scanning session as the echo signals are received. Additionally or alternatively, the ultrasound information may be stored temporarily in the memory 34 during a scanning session and processed in less than real-time in a live or off-line operation. An image memory 40 is included for storing processed frames of acquired ultrasound information that are not scheduled to be displayed immediately. The image memory 40 may comprise any known data storage medium, for example, a permanent storage medium, removable storage medium, etc.

The processor module 36 is connected to a user interface 42 that controls operation of the processor module 36 as explained below in more detail and is configured to receive inputs from an operator. The display 38 includes one or more monitors that present patient information, including diagnostic ultrasound images to the user for review, diagnosis and analysis. The display 38 may automatically display, for example, multiple planes from a three-dimensional (3D) ultrasound data set stored in the memory 34 or 40. One or both of the memory 34 and the memory 40 may store 3D data sets of the ultrasound data, where such 3D data sets are accessed to present 2D and 3D images. For example, a 3D ultrasound data set may be mapped into the corresponding memory 34 or 40, as well as one or more reference planes. The processing of the data, including the data sets, is based in part on user inputs, for example, user selections received at the user interface 42.

In operation, the system 20 acquires data, for example, volumetric data sets by various techniques (e.g., 3D scanning, real-time 3D imaging, volume scanning, 2D scanning with transducers having positioning sensors, freehand scanning using a voxel correlation technique, scanning using 2D or matrix array transducers, etc.). The data is acquired by moving the transducer 26, such as along a linear or arcuate path, while scanning a region of interest (ROI). At each linear or arcuate position, the transducer 26 obtains scan planes that are stored in the memory 34.

Figure 2:
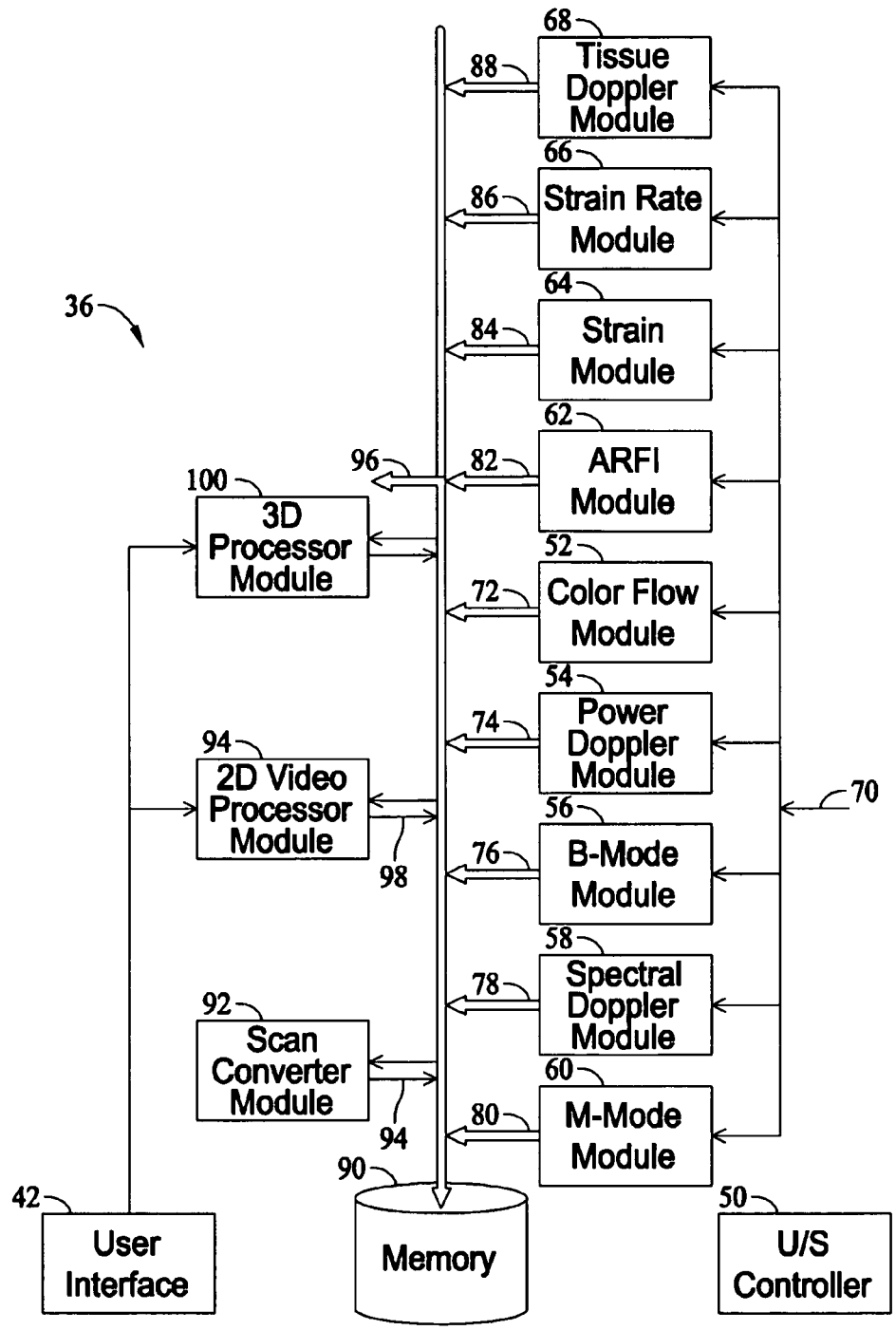
FIG. 2 is a block diagram of an ultrasound processor module of the diagnostic ultrasound system of FIG. 1 formed in accordance with an embodiment of the invention.

FIG. 2 illustrates an exemplary block diagram of the ultrasound processor module 36 of FIG. 1 formed in accordance with an embodiment of the present invention. The ultrasound processor module 36 is illustrated conceptually as a collection of sub-modules, but may be implemented utilizing any combination of dedicated hardware boards, DSPs, processors, etc. Alternatively, the sub-modules of FIG. 2 may be implemented utilizing an off-the-shelf PC with a single processor or multiple processors, with the functional operations distributed between the processors. As a further option, the sub-modules of FIG. 2 may be implemented utilizing a hybrid configuration in which certain modular functions are performed utilizing dedicated hardware, while the remaining modular functions are performed utilizing an off-the shelf PC and the like. The sub-modules also may be implemented as software modules within a processing unit.

The operations of the sub-modules illustrated in FIG. 2 may be controlled by a local ultrasound controller 50 or by the processor module 36. The sub-modules 52-68 perform mid-processor operations. The ultrasound processor module 36 may receive ultrasound data 70 in one of several forms. In the embodiment of FIG. 2, the received ultrasound data 70 constitutes I,Q data pairs representing the real and imaginary components associated with each data sample. The I,Q data pairs are provided to one or more of a color-flow sub-module 52, a power Doppler sub-module 54, a B-mode sub-module 56, a spectral Doppler sub-module 58 and an M-mode sub-module 60. Optionally, other sub-modules may be included such as an Acoustic Radiation Force Impulse (ARFI) sub-module 62, a strain module 64, a strain rate sub-module 66, a Tissue Doppler (TDE) sub-module 68, among others. The strain sub-module 62, strain rate sub-module 66 and TDE sub-module 68 together may define an echocardiographic processing portion.

Each of sub-modules 52-68 are configured to process the I,Q data pairs in a corresponding manner to generate color-flow data 72, power Doppler data 74, B-mode data 76, spectral Doppler data 78, M-mode data 80, ARFI data 82, echocardiographic strain data 82, echocardiographic strain rate data 86 and tissue Doppler data 88, all of which may be stored in a memory 90 (or memory 34 or image memory 40 shown in FIG. 1) temporarily before subsequent processing. The data 72-88 may be stored, for example, as sets of vector data values, where each set defines an individual ultrasound image frame. The vector data values are generally organized based on the polar coordinate system.

A scan converter sub-module 92 access and obtains from the memory 90 the vector data values associated with an image frame and converts the set of vector data values to Cartesian coordinates to generate an ultrasound image frame 94 formatted for display. The ultrasound image frames 94 generated by the scan converter module 92 may be provided back to the memory 90 for subsequent processing or may be provided to the memory 34 or the image memory 40.

Once the scan converter sub-module 92 generates the ultrasound image frames 94 associated with, for example, the strain data, strain rate data, and the like, the image frames may be restored in the memory 90 or communicated over a bus 96 to a database (not shown), the memory 34, the image memory 40 and/or to other processors (not shown).

As an example, it may be desired to view different types of ultrasound images relating to echocardiographic functions in real-time on the display 38 (shown in FIG. 1). To do so, the scan converter sub-module 92 obtains strain or strain rate vector data sets for images stored in the memory 90. The vector data is interpolated where necessary and converted into an X,Y format for video display to produce ultrasound image frames. The scan converted ultrasound image frames are provided to a display controller (not shown) that may include a video processor that maps the video to a grey-scale mapping for video display. The grey-scale map may represent a transfer function of the raw image data to displayed grey levels. Once the video data is mapped to the grey-scale values, the display controller controls the display 38, which may include one or more monitors or windows of the display, to display the image frame. The echocardiographic image displayed in the display 38 is produced from an image frame of data in which each datum indicates the intensity or brightness of a respective pixel in the display. In this example, the display image represents muscle motion in a region of interest being imaged.

Referring again to FIG. 2, a 2D video processor sub-module 94 combines one or more of the frames generated from the different types of ultrasound information. For example, the 2D video processor sub-module 94 may combine a different image frames by mapping one type of data to a grey map and mapping the other type of data to a color map for video display. In the final displayed image, the color pixel data is superimposed on the grey scale pixel data to form a single multi-mode image frame 98 that is again re-stored in the memory 90 or communicated over the bus 96. Successive frames of images may be stored as a cine loop in the memory 90 or memory 40 (shown in FIG. 1). The cine loop represents a first in, first out circular image buffer to capture image data that is displayed in real-time to the user. The user may freeze the cine loop by entering a freeze command at the user interface 42. The user interface 42 may include, for example, a keyboard and mouse and all other input controls associated with inputting information into the ultrasound system 20 (shown in FIG. 1).

A 3D processor sub-module 100 is also controlled by the user interface 42 and accesses the memory 90 to obtain spatially consecutive groups of ultrasound image frames and to generate three dimensional image representations thereof, such as through volume rendering or surface rendering algorithms as are known. The three dimensional images may be generated utilizing various imaging techniques, such as ray-casting, maximum intensity pixel projection and the like.

Figure 3:
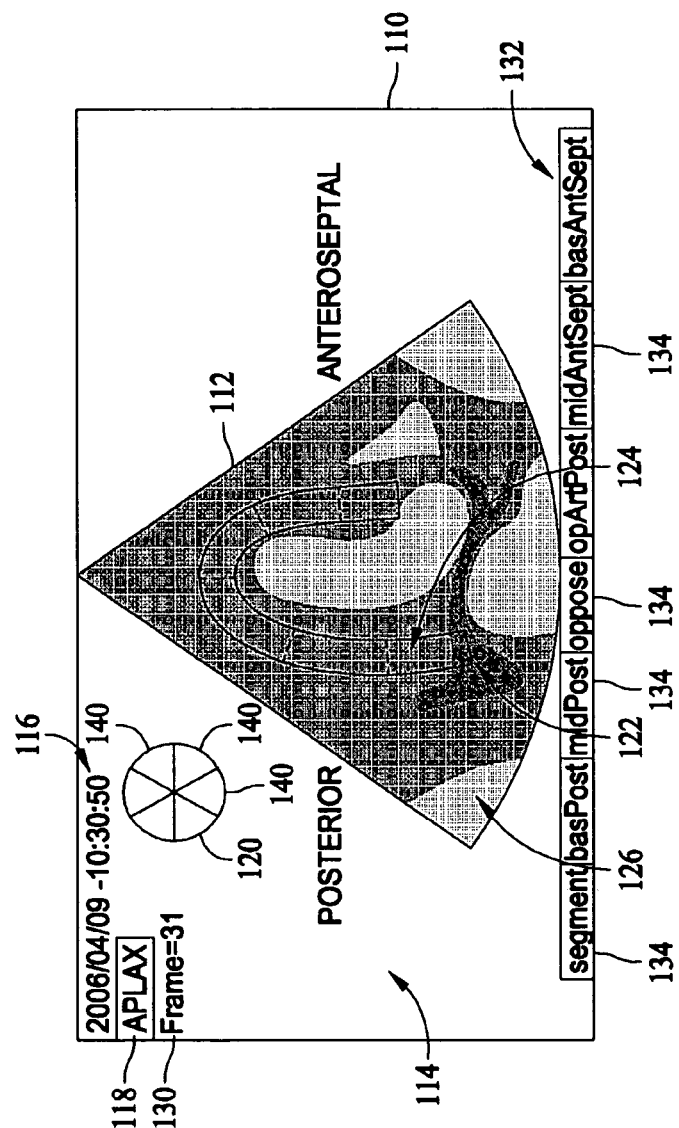
FIG. 3 illustrates a window presented on a display for displaying medical imaging information in accordance with an embodiment of the invention and having an overlay.

Various embodiments of the present invention provide indications on a screen display to associate or correlate information in different portions of the screen, for example, for visual correlation by a user when, for example, selecting points/regions and viewing images on the display 38 (shown in FIG. 1). FIG. 3 is an exemplary window 110 (or display panel) that may be presented on the display 38 or a portion thereof and controlled by the user interface 42 (shown in FIG. 1). For example, multiple windows may be provided on a divided single screen. The user may access different input means as part of the user interface 42, for example, a mouse, trackball and keyboard, among others, to move a cursor or marker within the window 110, for example, to select certain points or regions within the window 110 (e.g., point and click with a mouse).

The window 110 generally includes an image portion 112 and a non-image portion 114 that may provide different information relating to the image being displayed, the status of the system, etc. For example, the non-image portion 112 may include time and date information 116, an image type label 118 and a status indicator 120. More particularly, the time and date information 116 may show the current time and date or the time and date at which the image being displayed on the image portion 112 was acquired. The image type label 118 provides an indication of, for example, the view of the image being displayed, which in the exemplary window 110 is an Apical Long Axis (APLAX) view. The status indicator 120 provides an indication of the status of the current system processing and the overall system processing, for example, by the shading of different segments 140 of the status indicator as described in co-pending U.S. patent application entitled "USER INTERFACE AND METHOD FOR DISPLAYING INFORMATION IN AN ULTRASOUND SYSTEM" having Ser. No. 11/418,778 and assigned to assignee of the present invention.

Additional or alternate information may be provided, for example, frame number information 130 identifying the image frame being viewed in the image portion 112 and a legend 132 identifying portions of an image 126, for example, portions of a segmented overlay 122 having a plurality of segments 124. For example, as shown in FIG. 3, when displaying an image 126 of a heart, six segments may be provided to divide an outline defining an endocardial border and an epicardial border of the myocardium into different regions. In particular, the legend 132 may include a plurality of labels 134 corresponding to different segments 124 of the segmented overlay 122. The labels 134 may include an abbreviated description of the region of the image 126 identified by the corresponding segment 124. Each of the labels 134 may be provided in a separate text box that is color coded with the corresponding segment 124 having an outline in the same color. Essentially, each label 134 is an identifier for a corresponding segment 124. Thus, as shown in FIG. 3, six different colors may be used to color code and identify the labels 134 of the legend 132 with the corresponding segment 124.

Figure 4:
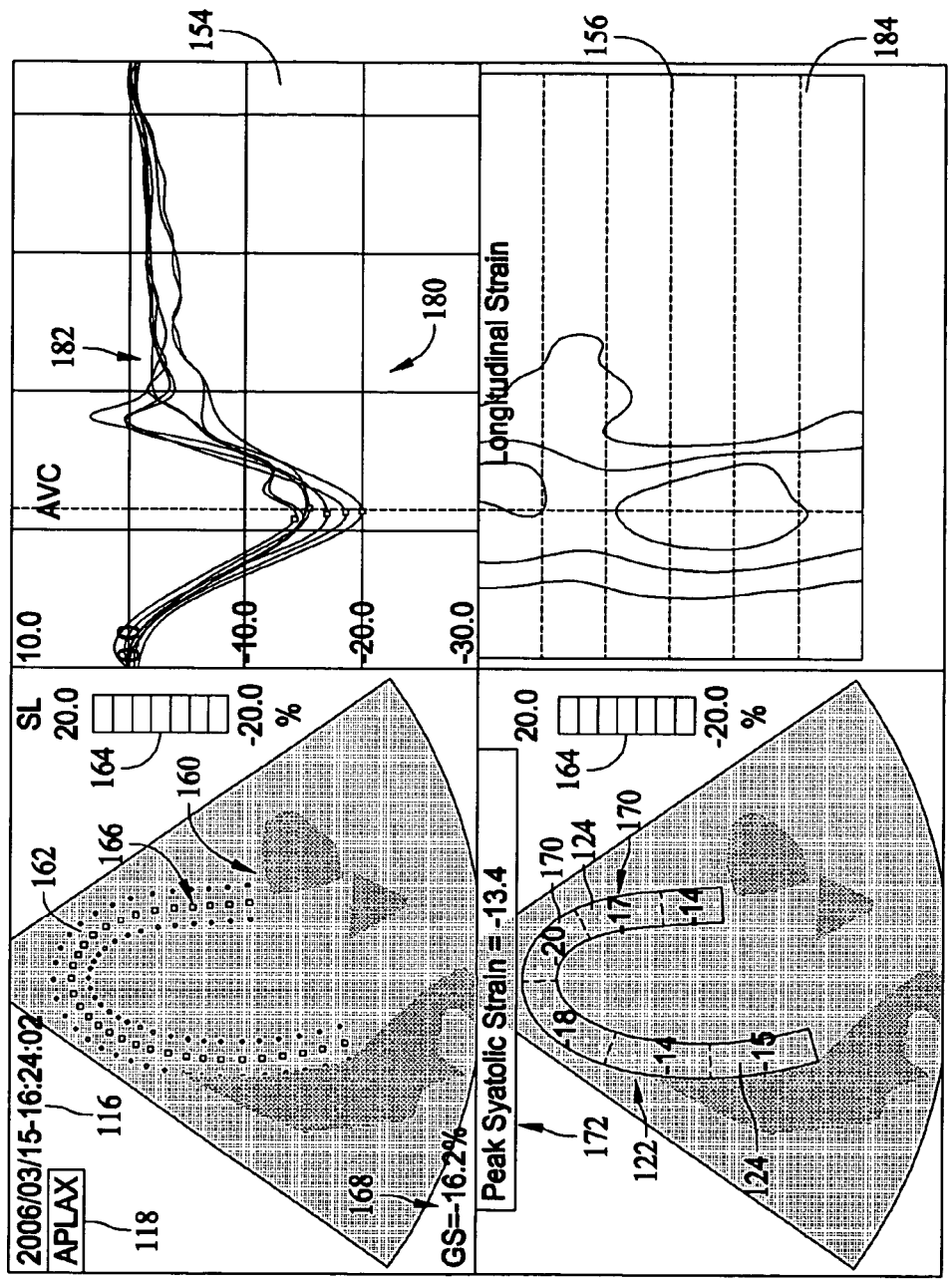
FIG. 4 illustrates a multi-window display for displaying medical imaging information in accordance with an embodiment of the invention.

The window 110 is merely exemplary of a display screen that may be provided to display medical image data according to various embodiments of the invention. However, different windows with different information may be provided on a plurality of displays or in different portions of a single display 38. For example, a display 38 may include a plurality of windows including a first window 150, a second window 152, a third window 154 and a fourth window 156 as shown in FIG. 4. The windows 150-156 may be configured to define a quad-view with the display 38 divided into four generally equal sized regions. In this embodiment, and when displaying, for example, an image of a heart, the first window 150 may be configured to display a moving image 160, for example, a continuously running cine loop of the heart in a particular view (e.g., Apical Long Axis View, two chamber view or four chamber view). The first window 150 may display the moving image 160 of the heart as a grayscale cine loop of a full heart cycle or a portion thereof. Alternatively, the image may be stopped to display a single image frame of the displayed heart.

The first window 150 may also include information overlaid on the moving image 160, for example, a color coded overlay 162 displayed as a function of time and defined by a color coded legend 164 showing a color coded scale representing different strain value or levels, such as, percentage levels. In one embodiment, the overlaid information is a local instantaneous strain value displayed as a function of time. For example, the local instantaneous strain value may be a percentage value based on a change in length of the heart muscle at a particular location, such as based on a percent of muscle contraction. The strain value may be calculated in any known manner using, for example, the strain sub-module 64 (shown in FIG. 2). The calculated strain values may be stored in a database that associates the strain value with a portion of the moving image 160 having the color coded overlay 162 and associated and identified, for example, by a pixel position in the first window 150. For example, calculated strain values may be stored in an addressable table wherein each address corresponds to a different displayed pixel or region of the color coded overlay 162. Accordingly, when a portion of the color coded overlay is selected, for example, with a marker 166 (e.g., virtual circle element) by moving the marker to that portion with a mouse of the user interface 42 (shown in FIG. 1), the instantaneous strain value for that region, as determined by the stored strain values, is displayed as strain value information 168. The strain value information 168 may represent, for example, a global strain (GS) value across the entire region represented by the color coded overlay 162 (e.g., the percentage change of the entire length of the region represented by the color coded overlay 162). Thus, the color coded overlay 162 may be a virtual map overlaid on a muscle portion of an image of the heart with the coloring corresponding to the colors of the color coded legend 164.

The second window 152 may be configured to display the segmented overlay 122 having the plurality of color coded segments 124 as described in more detail above in connection with FIG. 3. Each of the segments 124 may be defined by a different colored solid line generally defining an area (e.g., a rectangular area). The color coded legend 164 also may be provided similar to the first window 150. In this embodiment, an average strain value 170 is provided within each of the segments 124. In particular, an average strain value 170 as a function of time for the region defined by the segment 124 is displayed in the corresponding segment 124. For example, the average strain value at a particular time is calculated. The average strain value 170 may be calculated by averaging the instantaneous strain values stored in the database. Additionally, when a portion of the color coded overlay 162 in the first window 150 is selected, for example, with the marker 166 (e.g., virtual circle element) by moving the marker to that portion with a mouse of the user interface 42, a peak systolic strain value 172 is displayed in the second window 152 corresponding to the point or region where the marker 166 is positioned in the first window 150. Thus, when the marker 166 is placed at any point in the color coded overlay 162 in the first window 150, the peak systolic value 172 corresponding to that point is displayed in the second window 152. Alternatively, the peak systolic value 172 may be displayed in other regions of the display 38, for example, in the first window 150. It should be noted that the peak systolic value 172 in one embodiment is the peak systolic strain, and more particularly, the peak negative strain if the peak occurs during systole or end systolic strain if the peak occurs later. This value generally may be the strain value as a function of any time during the heart cycle.

It should be noted that other physiological parameters may be mapped as a function of time and displayed in one of the first and second windows 150 and 152, for example, a parametric peak systolic strain image with corresponding numeric values. Further, it should be noted that when a new or different view or image is displayed in one of the first and second windows 150 and/or 152, a new overlay or corresponding values are also displayed based on the new view or image. Additionally, if the image displayed is modified, for example, inverted, the overlay, color coding and corresponding text is also inverted. The inversion may be provided by remapping of the pixels in one of the first and second windows 150 and/or 152.

The third window 154 may be configured to display non-image data, for example, a graph 180 of a plurality of strain curves 182 plotted as a function of time. For example, the plurality of strain curves 182 may represent average strain as a function of time with each curve trace corresponding to a different segment 124 of the segmented overlay 122 displayed in the second window 152. Thus, in this example, six curve traces corresponding to the six segments 124 are generated and displayed in any known manner. In one embodiment, each of the curve traces of the plurality of strain curves 182 are provided in a different color corresponding to the color of the segment 124 (e.g., color of the outline of the segment 124) in the second window 152 to which the curve trace is related.

In operation, when a portion of the segmented overlay 122 in the second window 152 is selected, for example, when the marker 166 (e.g., virtual circle element) is moved into one of the segments 124 with a mouse of the user interface 42, the curve trace in the third window 154 corresponding to the selected segment 124 is highlighted. For example, a single one of the plurality of strain curves 182 corresponding to the segment 124 selected is highlighted, which may be, for example, to brighten the color of the trace, enlarge the trace line, change the color of the trace to another highlighted color (e.g., highlighted red), etc. In general, a visual indication of the single one of the plurality of strain curves 182 corresponding to the selected segment 124 is provided. Additionally, if the marker 166 is placed on one of the plurality of strain curves 182, the curve trace selected may be highlighted and the corresponding segment 124 in the second window 152 is highlighted or an average strain value displayed.

The fourth window 156 may be configured to display information or an image corresponding to the images in the first and second windows 150 and 152, for example, a color M-mode image 184. The color M-mode image 184 also may be displayed such that colors in the image correspond to the colored indications and color coding in the first, second and third windows 150, 152 and 154.

Figure 5:
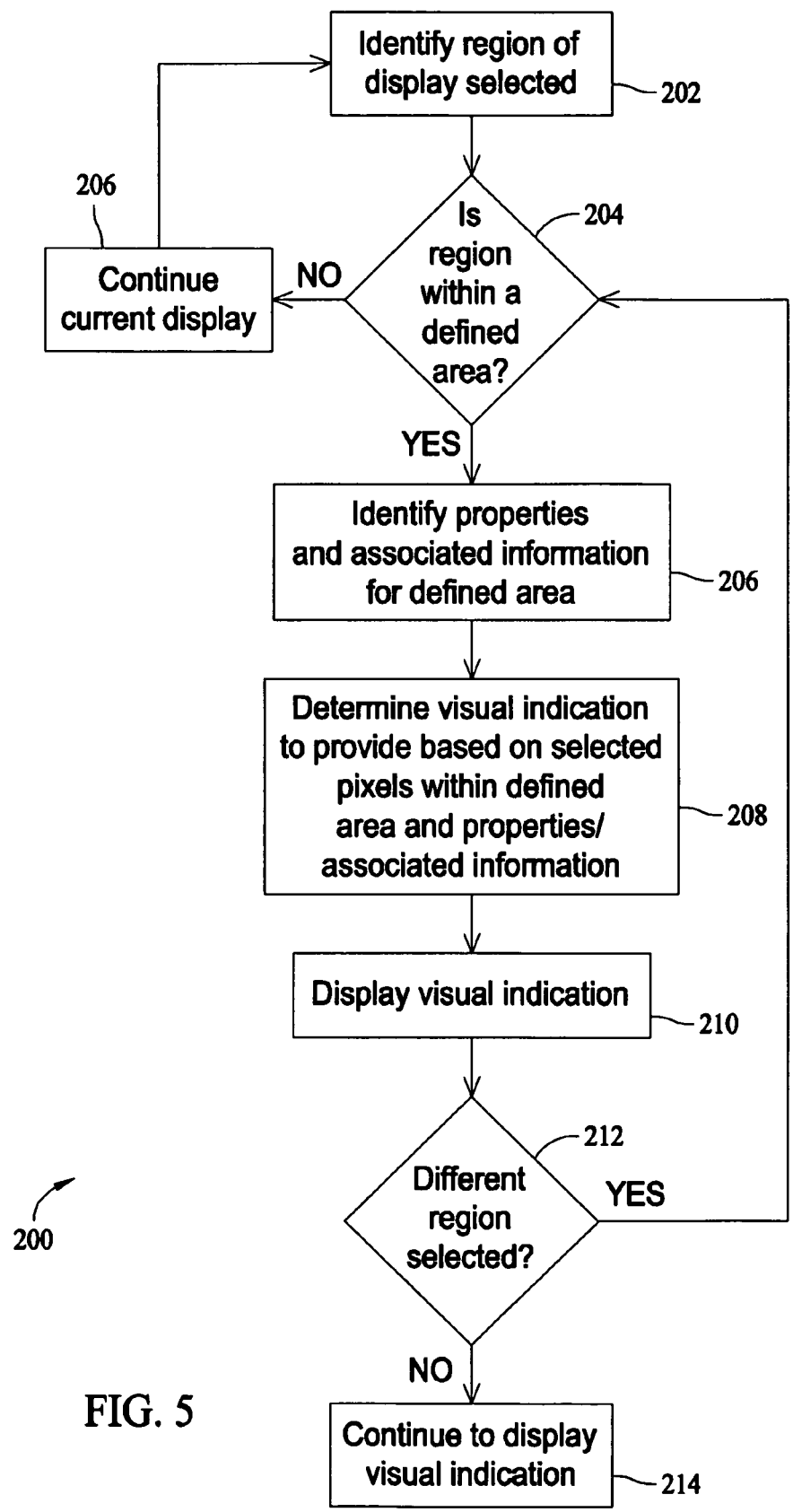
FIG. 5 is flowchart of a method in accordance with an embodiment of the invention to identify and associate information displayed in different portions of a display of a medical imaging system.

Various embodiments provide a method 200 as shown in FIG. 5 to identify and associate information displayed in different regions of a display of a medical imaging system, and more particularly, an ultrasound system. Specifically, at 202 a region within the display that is selected is identified. For example, the region wherein a marker or other visual selector is positioned by a user is identified. This may include, for example, identifying which of a plurality of windows on a screen contains the marker. Also, a determination may be made as to the different information displayed in the various regions, for example, the different images or views displayed. Thereafter, a determination is made as to whether the region is within a defined area at 204. This may include, for example, determining whether the region is within a segment 124 of the segmented overlay 124 in the second window 152, for example, whether pixels of the display 28 are within a segment 124 (all shown in FIG. 4). As another example, the determination at 204 may include determining whether the region is within a portion of the color coded overlay 162, for example, whether pixels of the display 28 are within a particular portion of the color coded overlay 162 (all shown in FIG. 4). The identification of selected regions or pixels at 202 and/or 204 may be performed using any known process, for example, associating a virtual marker with corresponding pixels within or encompassed by the virtual marker.

If at 204 a determination is made that the region is not within a defined area, then the current display is continued at 206. For example, the images and indications on the display are not changed and the method again identifies a selected region of the display. For example, the display may be sampled on a continuous or periodic basis to identify the position of, for example, a virtual marker. The display also may be sampled upon detecting movement of the virtual marker.

If at 204 a determination is made that the region is within a defined area, then at 206 the properties and associated information for the defined area are identified. For example, properties and associated information may be provided corresponding to each pixel or a group of pixels within a defined area. This information may include, for example, calculated data for that defined area. In the embodiment wherein myocardial images, etc. are displayed the information may include local instantaneous strain values, average/peak strain values for a segment and/or percentage strain value for the segment. The defined area also may include properties, such as that the area is linked or associated with another region of the display, for example, in another window. For example, information within a single segment in a segmented overlay in one window may be linked to a single curve trace in another window. As another example, information in a single segment in the segmented overlay may be associated with a legend or numerical value information displayed in one or more of the windows. Information that is correlated or associated may be identified by the same color in different windows.

The properties and associated information, for example, calculated and measured values may be stored in a database that associates the properties and information with the defined area, for example, a portion of a segmented map or a portion of a displayed image. The information may be stored in the database based on pixel association in the display, for example, pixels in each of the windows. The properties, such as links and associated information, including data values may be stored in an addressable table wherein each address corresponds to a different displayed pixel or region of the defined area. The visual indications to be provided, the linking, etc. may be predetermined and/or user defined.

Upon identifying the properties and associated information, then at 208, a determination is made as to visual indications to provide based on selected pixels within the defined area that correspond to the identified properties and associated information. The visual indications to provide may be based on selected pixels with the corresponding visual indications defined within the database by the stored properties and associated information. The visual indications may include, for example, displaying a data value in a portion of the display corresponding to the selected region and/or highlighting another portion of the display (e.g., in another window) corresponding to the selected region. The visual indications may include providing the visual indications showing related information as described above with respect to FIG. 4. For example, the defined area may be a segment of the segmented overlay corresponding to a single trace curve. The determined visual indication may be to highlight the curve trace corresponding to the selected segment. As another example, associated information, for example, a percentage strain value may be displayed if the defined area is within an instantaneous strain overlay. The information may be displayed in the same window or a different window than the selected region. The information may be linked and associated based on, for example, a mapping of the pixel data.

It should be noted that some of the information may be displayed continuously and some of the information may be displayed only when selected. For example, average strain values in each segment 124 of a segmented overlay 122 may be continuously displayed in the segmented overlay 122 or color-coding to associate segments 124 in a spatial view with physiological parameters graphed over time may be displayed as shown in FIG. 4. As another example, percentage strain values and highlighting of curve traces may be displayed only when a corresponding region is selected and a visual indication is to be provided.

The visual indication is then displayed at 210. Thereafter, a determination is made at 212 as to whether a different region is selected, for example, by movement of the virtual marker to another area of the display. If a different region is not selected, then at 214 the current visual indications continue to be displayed. If a different region is selected, then a determination is made at 204 as to whether the region is within a defined area and the process proceeds as described above.

Thus, various embodiments provide a display that includes visual indications that associate information displayed in different portions of the display. The visual indications may be provided continuously (e.g., color coding) or upon selecting a particular region of interest, which includes linking or associating information related to the selected region of interest.

While the invention has been described in terms of various specific embodiments, those skilled in the art will recognize that the invention can be practiced with modification within the spirit and scope of the claims.

What is claimed is:

1. A medical image display comprising:
a first region configured to display a medical image having color coded portions;
a second region configured to display non-image data related to the medical image displayed in the first region, the non-image data color coded to associate the non-image data with the color coded portions of the medical image; and
a color coded segment overlay superimposed on the displayed medical image, wherein the medical image is an image of a heart and the color coded segment overlay defines a myocardium of the heart and displays strain data for each segment within a corresponding portion of the color coded segment overlay.

2. A medical image display in accordance with claim 1 wherein the medical image is segmented with each segment having a different corresponding color.

3. A medical image display in accordance with claim 1 wherein the color coded portions define color coded segments of the myocardium of the displayed medical image, each segment having a differently colored solid outline and including a visual indication of an average strain value, and wherein the non-image data comprises a plurality of trace curves showing average strain data over time, each of the plurality of trace curves corresponding to a different color coded segment and colored in the same color as the colored outline of the corresponding color coded segment.

4. A medical image display in accordance with claim 1 wherein the medical image displayed in the first region is acquired from a region of interest by a medical imaging system constituting one of an MRI system, CT system and Ultrasound system.

5. A medical image display in accordance with claim 1 wherein the medical image displayed in the first region is acquired from a region of interest by an ultrasound system that processes acquired ultrasound information from a region of interest and prepares a frame of ultrasound information for display as the medical image.

6. A medical image display in accordance with claim 5, the ultrasound information containing at least one of the strain data and strain rate data, the color coded portions of the medical image being color coded based upon the values of at least one of the strain data and strain rate data.

7. A medical image display comprising:
a first region configured to display a medical image having color coded portions;
a second region configured to display non-image data related to the medical image displayed in the first region, the non-image data color coded to associate the non-image data with the color coded portions of the medical image, wherein the non-image data comprises physiologic parameter data graphed over time; and
a single trace curve corresponding to each color coded portion of the displayed medical image with each single trace curve colored the same as the corresponding color coded portion of the displayed medical image.

8. A medical image display in accordance with claim 7 wherein the single trace curve corresponding to a color coded portion of the displayed medical image is highlighted upon selection by a user of the corresponding color coded portion.

9. A medical image display comprising:
a first region configured to display a medical image having color coded portions; and
a second region configured to display non-image data related to the medical image displayed in the first region, the non-image data color coded to associate the non-image data with the color coded portions of the medical image, wherein the displayed medical image is configured in a color coded segmental view and the non-image data comprises a plurality of curves defining a graph of physiologic parameters segmented into color bands corresponding to the segments of the color coded segmental view.

10. A medical image display comprising:
a first region configured to display a medical image having color coded portions;
a second region configured to display non-image data related to the medical image displayed in the first region, the non-image data color coded to associate the non-image data with the color coded portions of the medical image; and a third region configured to display the medical image with a color coded overlay superimposed on the medical image, the color coded overlay defining strain values displayed as a function of time.

11. A medical image display in accordance with claim 10 further comprising a color coded legend identifying a strain percentage range corresponding to the color coded overlay.

12. A medical image display in accordance with claim 10 further comprising a strain value displayed and associated with a selected region in one of the color coded overlay in the third region and the color coded portions in the first region.

13. A medical image display in accordance with claim 12 wherein the strain value is automatically updated based on the region selected.

14. A medical image display in accordance with claim 10 wherein the first, second and third regions define separate windows in a quad-view arrangement.

15. A medical image display in accordance with claim 10, wherein the strain values constitute one of strain data and strain rate data.

16. A method to associate medical information displayed in different regions of a display of a medical imaging system, the method comprising:
   color coding data in different regions of the display, wherein the data comprises a trace curve corresponding to one of a plurality of segmented color coded portions of a displayed medical image;
   associating data in the different regions based on the color coding; and
   displaying at least one visual indication corresponding to the color coded data in the different regions.

17. A method in accordance with claim 16 wherein the displaying at least one visual indication comprises highlighting corresponding data.

18. A method in accordance with claim 16 wherein the displaying at least one visual indication further comprises displaying a dynamic value corresponding to a selected region.

19. A method in accordance with claim 16 further comprising displaying an ultrasound image of a heart and wherein the color coded data comprises segmented strain data for a defined myocardium.

20. A method in accordance with claim 16 further comprising acquiring the medical image displayed in the first region from a region of interest using a medical imaging system constituting one of an MRI system, CT system and ultrasound system.

21. A method in accordance with claim 16 further comprising acquiring the medical image displayed in the first region is from a region of interest using an ultrasound system that processes ultrasound information from a region of interest and prepares frames of ultrasound information for display as the medical image.

22. A method in accordance with claim 21, wherein the ultrasound information contains at least one of strain data and strain rate data, said method further comprising color coding the color coded portions of the medical image based upon the values of at least one of the strain data and strain rate data.

* * * * *